US011975138B2

(12) United States Patent
Moloney et al.

(10) Patent No.: US 11,975,138 B2
(45) Date of Patent: May 7, 2024

(54) APPARATUS FOR GENERATING AEROSOL FROM AN AEROSOLIZABLE MEDIUM, AN ARTICLE OF AEROSOLIZABLE MEDIUM AND A METHOD OF OPERATING AN AEROSOL GENERATING APPARATUS

(71) Applicant: NICOVENTURES TRADING LIMITED, London (GB)

(72) Inventors: Patrick Moloney, London (GB); Justin Han Yang Chan, London (GB)

(73) Assignee: NICOVENTURES TRADING LIMITED, London (GB)

( * ) Notice: Subject to any disclaimer, the term of this patent is extended or adjusted under 35 U.S.C. 154(b) by 847 days.

(21) Appl. No.: 15/733,695

(22) PCT Filed: Mar. 27, 2019

(86) PCT No.: PCT/EP2019/057721
§ 371 (c)(1),
(2) Date: Sep. 29, 2020

(87) PCT Pub. No.: WO2019/185715
PCT Pub. Date: Oct. 3, 2019

(65) Prior Publication Data
US 2021/0015167 A1 Jan. 21, 2021

(30) Foreign Application Priority Data
Mar. 29, 2018 (GB) ...................... 1805234

(51) Int. Cl.
*A61M 11/04* (2006.01)
*A24F 40/20* (2020.01)
(Continued)

(52) U.S. Cl.
CPC ............ *A61M 11/042* (2014.02); *A24F 40/40* (2020.01); *A24F 40/50* (2020.01); *A24F 40/53* (2020.01); *A24F 40/60* (2020.01); *A24F 40/20* (2020.01)

(58) Field of Classification Search
CPC .......... A24F 40/53; A24F 40/40; A24F 40/50; A24F 40/60; A24F 40/46; A24F 40/51; A24F 40/20; A61M 11/042
(Continued)

(56) References Cited

U.S. PATENT DOCUMENTS

2006/0196518 A1 9/2006 Hon
2009/0272379 A1 11/2009 Thorens et al.
(Continued)

FOREIGN PATENT DOCUMENTS

CA 2999210 A1 3/2017
CN 1280661 A 1/2001
(Continued)

OTHER PUBLICATIONS

"Extended European Search Report Received for Patent Application No. 20204750.2, dated Jun. 1, 2021", 13 pages.
(Continued)

*Primary Examiner* — Gary F Paumen
(74) *Attorney, Agent, or Firm* — Burr & Forman LLP

(57) ABSTRACT

An aerosol generating device for receiving an aerosol generating article includes an electrical circuit including a controller for determining a change in an electrical property of the circuit. The change in the electrical property of the circuit is caused by the user interacting with an aerosol generating article received by the device.

19 Claims, 5 Drawing Sheets

(51) Int. Cl.
*A24F 40/40* (2020.01)
*A24F 40/50* (2020.01)
*A24F 40/53* (2020.01)
*A24F 40/60* (2020.01)

(58) Field of Classification Search
USPC .................................................. 131/328, 329
See application file for complete search history.

(56) References Cited

U.S. PATENT DOCUMENTS

| | | |
|---|---|---|
| 2011/0277756 A1 | 11/2011 | Terry et al. |
| 2013/0037041 A1 | 2/2013 | Worm et al. |
| 2014/0107815 A1 | 4/2014 | Lamothe |
| 2014/0123989 A1 | 5/2014 | Lamothe |
| 2014/0246020 A1 | 9/2014 | Minskoff et al. |
| 2014/0261491 A1* | 9/2014 | Hawes ..................... A61L 9/037 392/395 |
| 2015/0020825 A1 | 1/2015 | Galloway et al. |
| 2015/0181945 A1 | 7/2015 | Tremblay |
| 2015/0313287 A1 | 11/2015 | Verleur et al. |
| 2015/0320114 A1 | 11/2015 | Wu |
| 2016/0029697 A1 | 2/2016 | Shafer |
| 2016/0158782 A1 | 6/2016 | Henry et al. |
| 2016/0302488 A1 | 10/2016 | Fernando et al. |
| 2016/0360785 A1* | 12/2016 | Bless .................. H05B 1/0244 |
| 2017/0020191 A1 | 1/2017 | Lamb et al. |
| 2017/0027234 A1* | 2/2017 | Farine ..................... A24F 40/53 |
| 2017/0094998 A1* | 4/2017 | Bernauer ................ A24F 40/70 |
| 2017/0258142 A1 | 9/2017 | Hatton et al. |
| 2018/0070636 A1* | 3/2018 | Ruscio ..................... A24F 40/40 |
| 2018/0077967 A1 | 3/2018 | Hatton et al. |
| 2019/0045837 A1* | 2/2019 | Spencer ................ A24D 1/002 |

FOREIGN PATENT DOCUMENTS

| | | |
|---|---|---|
| CN | 1541577 A | 11/2004 |
| CN | 103929988 A | 7/2014 |
| CN | 103974635 A | 8/2014 |
| CN | 106455707 A | 2/2017 |
| CN | 206923669 U | 1/2018 |
| EP | 2399636 A1 | 12/2011 |
| EP | 3229622 A1 | 10/2017 |
| EP | 3391760 A1 | 10/2018 |
| JP | 2014525237 A | 9/2014 |
| JP | 2017510270 A | 4/2017 |
| JP | 3212228 U | 8/2017 |
| RU | 2367089 C2 | 9/2009 |
| RU | 2643603 C2 | 2/2018 |
| RU | 2644314 C2 | 2/2018 |
| RU | 2647805 C2 | 3/2018 |
| WO | 9920940 A1 | 4/1999 |
| WO | 2011137453 A2 | 11/2011 |
| WO | 2012027350 A2 | 3/2012 |
| WO | 2015082560 A1 | 6/2015 |
| WO | 2015140312 A1 | 9/2015 |
| WO | 2015168828 A1 | 11/2015 |
| WO | 2016009202 A1 | 1/2016 |
| WO | 2016101202 A1 | 6/2016 |
| WO | 2017011419 A1 | 1/2017 |
| WO | 2017051011 A1 | 3/2017 |
| WO | 2017109868 A1 | 6/2017 |
| WO | 2017137138 A1 | 8/2017 |
| WO | 2017141017 A1 | 8/2017 |
| WO | 2017205692 A1 | 11/2017 |
| WO | 2017207442 A1 | 12/2017 |
| WO | 2018027189 A3 | 3/2018 |
| WO | 2018047095 A1 | 3/2018 |
| WO | 2019003166 A1 | 1/2019 |
| WO | 2019185715 A1 | 10/2019 |
| WO | 2019185748 A1 | 10/2019 |

OTHER PUBLICATIONS

"International Preliminary Report on Patentability Received for Patent Application No. PCT/EP2019/057721, dated Oct. 8, 2020", 10 pages.
"International Search Report and Written Opinion received for PCT Patent Application No. PCT/EP2019/057721, dated Jun. 14, 2019", 13 pages.
"Office Action and Search Report received for Chinese Patent Application No. 201980022425.3, dated Jun. 2, 2023", 15 pages. (12 pages of English Translation and 3 pages of Official).
"Office Action Received for Australian Patent Application No. 2019246399, dated Sep. 7, 2021", 9 pages.
"Office Action received for Chinese Patent Application No. 201980022425.3, dated Dec. 22, 2022", 13 pages (9 pages pf English Translation and 4 pages of Official Search Report).
"Office Action Received for New Zealand Patent Application No. 768072, dated Sep. 13, 2021", 3 pages.
"Office Action Received for Russian Patent Application No. 2020135636, dated Apr. 6, 2021", 2 pages (Official).
"Partial European Search Report Received for Patent Application No. 20204750.2, dated Mar. 1, 2021", 11 pages.
"Reason for Refusal Received for Japanese Patent Application No. 2020-182701, dated Jun. 7, 2022", 9 pages (4 pages pf English Translation and 5 pages of Official).
"Request for the Submission of an Opinion received for Korean Application No. 10-2020-7028028 dated Jan. 20, 2023", 11 pages. (6 pages of English Translation and 5 pages of Original).
"Search Report Received for Russian Patent Application No. 2020131747, dated Apr. 14, 2021", 3 pages (Official).
"Touch Switch", Available at URL :<https://en.wikipedia.org/wiki/Touch_switch>, May 5, 2019, 3 pages.
Lazaridis, Giorgos , "How Touch Buttons Work", Available at URL: <http://www.pcbheaven.com/wikipages/How_a_Touch_Button_works/?p=1>, Jan. 2, 2011, 8 pages.

* cited by examiner

APPARATUS FOR GENERATING AEROSOL FROM AN AEROSOLIZABLE MEDIUM, AN ARTICLE OF AEROSOLIZABLE MEDIUM AND A METHOD OF OPERATING AN AEROSOL GENERATING APPARATUS

PRIORITY CLAIM

The present application is a National Phase entry of PCT Application No. PCT/EP2019/057721, filed Mar. 27, 2019, which claims priority from GB Patent Application No. 1805234.0, filed Mar. 29, 2018, each of which is hereby fully incorporated herein by reference.

TECHNICAL FIELD

The present disclosure relates to aerosol generating device and to an article for use with an aerosol generating device.

BACKGROUND

Smoking articles such as cigarettes, cigars and the like burn tobacco during use to create tobacco smoke. Attempts have been made to provide alternatives to these tobacco-burning articles which release compounds from a material without burning. Examples of such products are so-called heat-not-burn products which release compounds by heating, but not burning, the material. The material may be, for example, tobacco or may be a non-tobacco material, which may or may not contain nicotine.

SUMMARY

According to a first aspect of the present disclosure, there is provided an aerosol generating device for receiving an aerosol generating article, wherein the device comprises an electrical circuit comprising a controller for determining a change in an electrical property of the circuit, and wherein the change is caused by the user interacting with an aerosol generating article received by the device.

The change in the property of the circuit may be caused by the user contacting the aerosol generating article. The article may comprise a conductive material and the change in the circuit may be caused by the user interacting with the conductive material. The change may be caused by the user contacting and thereby electrically grounding the conductive material. The change may be a change in the capacitance of the circuit and the controller may be configured to detect the change in capacitance by detecting a change in the time constant of the circuit. The device may be configured to evaluate a detected change in the property of the circuit to provide an indication of whether the article received in the device is of a predetermined type. The controller may be configured to prevent use of the device when the detected change in property of the circuit indicates that the article received in the device is not an approved article.

According to a second aspect of the present disclosure, there is provided an aerosol generating article for an aerosol generating device according to the first aspect of the disclosure, wherein the article comprises a conductive material and the conductive material comprises a first portion for interacting with a user when the user is in contact with the article and a second portion for electromagnetically interacting with the aerosol generating device.

The conductive material may be at least partially arranged at an external surface of the article such that it may be directly contacted by a user. The conductive material may be arranged so that no part of the material is directly contactable by the user.

According to a third aspect of the present disclosure, there is provided a method of detecting user interaction with an article inserted into a device according to the first aspect of the disclosure, wherein the method comprises detecting a change in a property of the electrical circuit when a user interacts with the article.

The method may comprise detecting a change in capacitance of the circuit when the user interacts with a conductive material in the article. The method may comprise comparing the change to the property of the circuit to a list of at least one value and enabling the device for use when the change to the property of the circuit corresponds with the at least one value.

Further features and advantages of the disclosure will become apparent from the following description of embodiments of the disclosure, given by way of example only, which is made with reference to the accompanying drawings.

DETAILED DESCRIPTION

Figure 1:
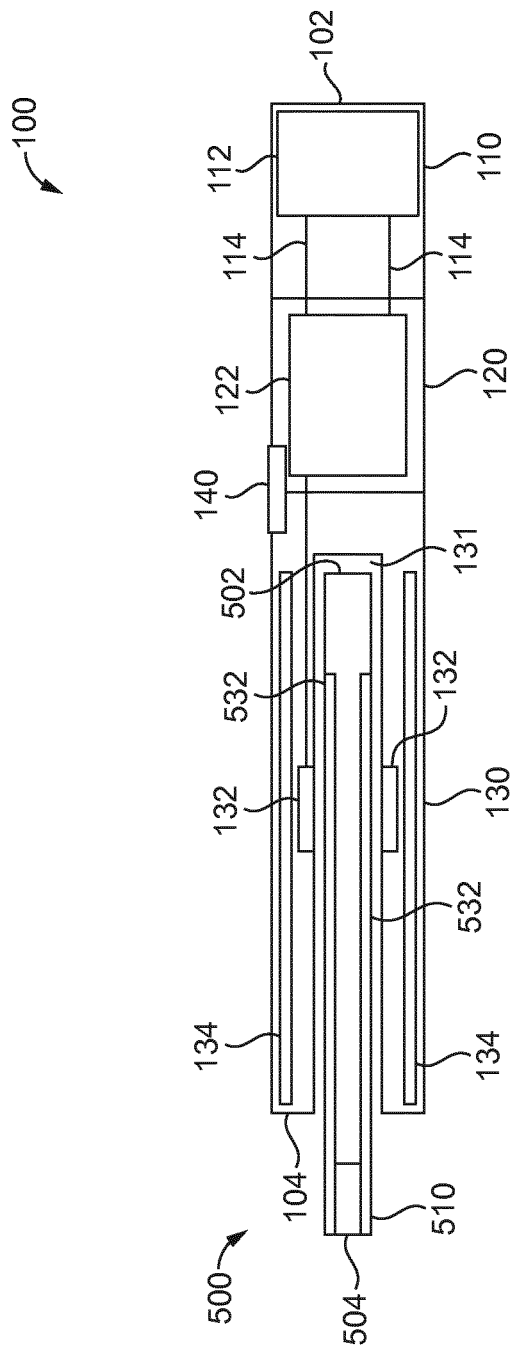
FIG. 1 shows a longitudinal cross-sectional view of an aerosol generating device and an aerosol generating article.
Figure 2:
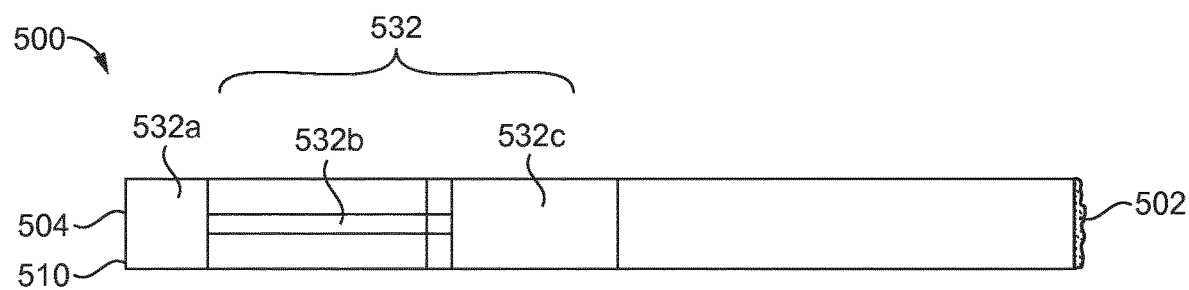
FIG. 2 shows a partial cross-sectional side view of a first example aerosol generating article.

Referring to FIG. 1 there is shown a longitudinal cross-sectional view of an aerosol generating device 100. The aerosol generating device 100 has a power compartment 110 which houses a power source 112 and conducting elements 114 for conducting energy through the device 100. In an example, the power source 112 is a source of electrical energy, such as a battery, and the power source 112 may be, for example, a rechargeable battery or a disposable battery. The conducting elements 114 may be wires or the like. The power compartment 110 is located towards the distal end 102 of the device 100 in the example shown in FIG. 1.

The device 100 has a controller compartment 120 which houses a controller 122. The controller 122 controls the operation of the device 100 based on, for example information received from at least one sensor such as a puff sensor (not shown) located in the device 100 or based on requests made by a user of the device 100, for example via user input means 140. The device 100 is configured to detect a change in an electrical property of an electrical circuit formed at least in part by the battery 112, the conducting elements 114 and the controller 122.

The device 100 has an article receiving compartment 130 arranged towards a proximal end 104 of the device 100. The article receiving compartment 130 defines a chamber 131 into which an article 500 may be received. The article receiving compartment 130 comprises a conductive surface 132 and a heating element 134. In the example of FIG. 1, conductive surface 132 is a single plate of conductive material. In other examples, more than one conductive surface, for example more than one conductive plate may be used.

The conductive surface 132 is for registering a change in the local environment of the chamber 131. That is, the conductive surface 132 is for registering the insertion of an article 500 into the chamber 131 and registering a change in an electrical property of the article 500 when inserted in the chamber 131.

The conductive surface 132 is part of the circuit formed at least in part by battery 112, the conductive elements 114 and the controller 122. The conductive surface 132 is configured to effect a change in an electrical property of the circuit when a change in the local environment of the chamber 131 is registered. For example, the conductive surface 132 is configured to effect a change in an electrical property of the circuit when the article 500 is inserted into the chamber 131. The conductive surface 132 is configured to cause a change in an electrical property of the circuit when the user interacts with the article 500 when the article 500 is inserted in the chamber 131, as will be discussed in more detail below. As such, the circuit formed by the power source 112, the conductive elements 114, the controller 122 and the conductive surface 132 forms a sensing circuit for sensing the insertion of an article 500 and for sensing user interaction with the article 500 when inserted in the device 100.

The conductive surface 132 is arranged to be affected by a change in the electromagnetic environment near the conductive surface 132. For example, the conductive surface 132 may be arranged to be affected by the insertion of conductive material into the chamber 131. When the conductive surface 132 is affected by user-related interaction, such as may occur during insertion of the article 500 into the chamber 131, the capacitance of the circuit may be affected.

The example article 500 shown in FIG. 1 is elongate in form and has a distal end 502 which is inserted into the chamber 131 and a proximal end 504 which is to be received in the mouth of a user. The article 500 has a mouthpiece 510 arranged at its proximal end 504. The mouthpiece 510 may have a filter or the like for selectively removing elements from the aerosol generated prior to inhalation by the user. In other examples, the article 500 may not be elongate in form and may take any suitable form and may, for example, not comprise a mouthpiece 504. The article 500 has a conductive material 532, which in this example extends along a length of the article 500. In the example of FIG. 1, the conductive material 532 extends from the proximal end 504 along the majority of the length of the article 500. In other examples, the conductive material 532 may extend along any portion of a length of the article 500, for example for only a minority of the length of the article.

The conductive material 532 is arranged so that, upon full insertion of the article 500 into the device 100, at least a portion of the conductive material 532 is arranged to be near to the conductive surface 132 of the device 100, such that the conductive material 532 can electromagnetically interact with the conductive surface 132.

The conductive surface 132 and/or the conductive material 532 may comprise any suitable conductive material, for example aluminum, conductive ink, or graphite.

In use, the user inserts the article 500 into the chamber 131 and at least a portion of the conductive surface 132 and conductive material 532 are arranged in a proximity to one another such that they may electromagnetically interact with one another. When arranged at such a proximity to one another, the first conductive surface 132 and the second conductive surface 532 may together have a first capacitance C0.

When the user contacts the article 500 received in the device 100 the user changes a property of the circuit. For example, the capacitance of the circuit may be changed by user interaction with the article 500. The change may be caused by the user contacting the conductive material 532 in the article 500, and thereby acting to electrically ground the article 500, or by the user otherwise interacting with the conductive material 532 such as deforming it through holding the article 500, or by a capacitive coupling effect between the user and the conductive material 532 of the article. The interaction of the user with the conductive material 532 may act to change the capacitance of circuit due to changing the capacitance at the conductive surface 132 and conductive material 532, for example to a second capacitance value C2. The change in capacitance from C0 to C2 may be detected by the controller 122.

Utilizing the effect of a user interacting with an article received by the device 100 may allow for a relatively large change in the electrical property of the circuit to be produced. For example, a relatively small change in capacitance in the circuit may be produced by insertion of an article which is not significantly affected by user interaction. In examples described herein, the user's interaction with the article 500 may amplify the change in the electrical property produced in the electrical circuit. For example, by grounding the conductive material 532 or producing a capacitance coupling between the user and the article 500, a larger change in the capacitance of the circuit may be produced than that produced by insertion of an article which is not affected by user interaction. The larger magnitude of the change may allow more reliable detection. In turn, this may allow the controller 122 to more accurately determine a property of the article 500, for example by providing a more reliable value for comparison to a list of pre-determined values, as will be described below.

The controller 122 may compare a detected change in capacitance when an article 500 is inserted with a database of capacitance values. In this way, the controller 122 may obtain an indication of whether the inserted article 500 is of a predetermined type. For example, the controller 122 may determine whether the article 500 is an article which is approved for use with the device 100 by the manufacturer by comparing the change in capacitance to a detected first capacitance C0 with a list of predetermined capacitance values which are associated with approved articles. If the detected capacitance matches a value from the list of predetermined values then the controller 122 may determine that the article 500 is approved for use and may be configured to enable use of the device 100. In preferred examples, the controller 122 may be configured to prevent use of the device 100 when the detected capacitance indicates that the article 500 is not approved for use.

As mentioned above, the controller 122 is also configured to detect a change in the capacitance of the conductive surface 132 and the conductive material 532 to a second capacitance value C2 due to a user interacting with the conductive material 532. The detected change in capacitance may be used to provide an indication of the type of article 500 inserted into the device 100 by comparing to a database of capacitance values, as described in the preceding paragraph. The change in capacitance of the circuit due to user interaction with an article 500 inserted in the device, in preferred examples, is used to determine whether an article 500 is of a predetermined type, for example, whether the article 500 is one which is approved for use by the manufacturer of the device 100. The device 100 may be enabled or not enabled, depending on whether an inserted article 500 is determined to be approved or not.

In some implementations, articles that have different aerosolizable material (i.e., material providing different flavored aerosols or different strengths of flavor/active substances) may be provided with different conductive materials that effect the properties of the electronic circuitry in different ways when a user interacts with the article 500. For example, a change in capacitance by a certain first amount may be indicative of one flavor of aerosolizable material, whereas a change in capacitance by a certain second amount may be indicative of another flavor of aerosolizable material. The controller 122 may be configured to not only detect a change in capacitance but also to quantify a change in capacitance and associate the change with a given article 500. The controller 122 may take enable the device to take different actions based on the magnitude of the change in capacitance.

In some examples, the device 100 may detect the length of time that a user is in contact with the article 500 while it is inserted in the device 100 via detection of a change in capacitance. The device 100 may, in some examples, detect a location at which the article 500 has been contacted by a user by measuring a change in capacitance and comparing to a reference value. In some examples, the device 100 may infer the duration of a puff by a user by detecting contact with the user's lips and the duration of such contact.

Once the device 100 is enabled, the controller 122 may instruct the power source 112 to provide energy to the heating element 134. The heating element 134 may be a resistive, chemical or inductive heater or the like. Activation of the heating element 134 may be based on the detection of the initiation of a smoking session by a puff sensor in the device 100. Alternatively, the user may select activation of the heating element 134 via an interface 140 on the device 100 after the device 100 has entered the operational state. The user may be informed via the interface 140 on the device 100 that the device 100 has entered the operational state.

In some examples, a detected change in capacitance may be used to provide an indication that a user is in contact with the article 500, and may act to indicate that the user is using the device 100. For example, an indication of use of the device 100 by the user may be used by the controller 122 to keep the device 100 in operation, and the controller 122 may be configured to change a factor of the operation of the device 100 when use of the device 100 (through a detected change of capacitance) has not been detected for a predetermined length of time. For example, the controller 122 may be configured to deactivate the device 100 when it detects that a user has not contacted the article 500 for a time period such as 4 minutes, or 1 minute.

The device 100 may require that a change in capacitance which is associated with when an approved article is contacted by a user is detected at regular intervals to keep the device 100 in operation. The device 100 may be enabled for the typical time required for a smoking session. In an example, the device 100 is enabled for around 4 minutes. In an alternative example, the device 100 is enabled for a shorter time. An advantage associated with enabling the device 100 for a shorter time period is that if attempts to circumvent the prevention features of the device 100 have led to the device 100 being enabled despite use of a non-approved article, such attempts would need to be repeated throughout the smoking session. This would make circumventing the prevention features of the device 100 more cumbersome for any person attempting to do so.

In other examples, the change in capacitance to C2 may act as a wake-up signal for the device. For example, the device may be provided nominally at a low power state (either by default or via activation of a hard on/switch, e.g., a user actuatable button provided on a surface of the device). In the low power state, the functions of the device may be limited, but the controller 122 is configured to detect changes in capacitance. As a user inserts the article 500 into the device, they contact the article 500 and thus couple the article to ground. Accordingly, when the article 500 is fully inserted, the capacitance C2 is detected by the controller 122. The controller 122 is configured, upon detecting the capacitance C2 for the first time, is configured to transition the device from a low power to a higher power state (i.e., a state in which functions of the device are not restricted). For instance, this might cause power to be supplied to the heater, or it might cause power to be supplied to a display screen on the device. In this way, the device can transition from a low power to a high-power state based on detection of a certain capacitance value indicative of the user interacting with the article 500.

Examples of articles 500 for use with the device 100 of FIG. 1 are shown in FIGS. 2 to 5. The article 500 shown in FIG. 2 has a distal end 502 for insertion into the device 100 of FIG. 1 and a proximal end 504 with a mouthpiece 510 for insertion into the mouth of a user. The conductive material 532 has a number of connected portions 532a, 532b, 532c.

The first portion 532a of the conductive material 532 is arranged at the proximal end 504 of the article 500. The first portion 532a is located near the mouthpiece 510 and may surround a portion of the mouthpiece 510. The first portion 532a is arranged so that the user may interact with the surface when holding the article 500 in the fingers or in the mouth during use. The first portion 532a registers the interaction of the user with the article 500 and a change is detected by the controller 122.

The first portion 532a is connected to a second portion 532b of the conductive material 532. The second portion 532b is a connecting portion between the first portion 532a and the third portion 532c of the conductive material 532. The second portion 532b is thinner than the first portion 532a and third portion 532c in the example shown in FIG. 2. The second portion 532b pervades any changes to the first portion 532a through to the third portion 532c.

The third portion 532c is arranged in a location to be within a proximity of the conductive surface 132 of the device 100. This may be towards the center of the article 500 or towards the distal end 502 of the article 500. The third portion 532c is of a size such that electrical changes to the first portion 532a are transmitted clearly to the first conductive surface 132 of the device 100.

Each portion of the conductive material 532 of the article 500 can be located either internally or externally of the article 500, for example a portion such as the third portion 532c may be located internally of the article 500 and may be circumscribed by an outer layer of the article 500 such as a paper outer layer. Whether portions of the conductive material 532 are located internally of externally may impact the clarity of signal transmitted to the circuit of the device 100, with externally located conductive material 532 generally having better clarity of signal. The clarity of signal to the circuit of the device 100 may also be affected by the size or area of the various portions of the conductive material 532. In examples where the conductive material 532 is on an external surface of the article 500 the area of conductive material 532 may be reduced in comparison to an arrangement wherein the conductive material 532 is internal to the article 500 while maintaining a comparable signal clarity.

In examples where the conductive material 532 is configured to be directly contacted by a user, the first portion 532a should not be so small that the user may hold and use the article 500 without contacting the conductive material 532. In the example shown in FIG. 2, the first portion 532a is external but the second and third portions 532b, 532c are internal.

Figure 3:
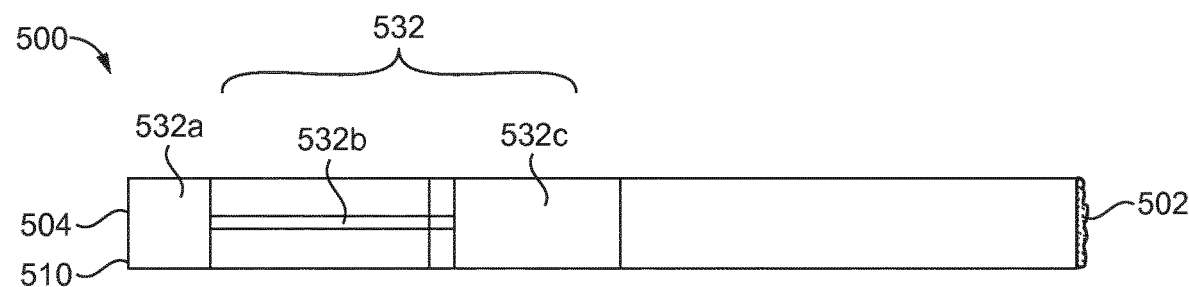
FIG. 3 shows a partial cross-sectional side view of a second example aerosol generating article.

Referring now to FIG. 3, there is shown an example of an article 500 for use with the device 100 of FIG. 1. The article 500 shown in FIG. 3 has similar features to the article 500 shown in FIG. 2. Where features are broadly the same across examples, the same reference numerals have been used and the description will not be repeated.

All three portions 532a, 532b, 532c of the conductive material 532 are internal in the example shown in FIG. 3. As mentioned above, the first portion 532a of the article 500 in FIG. 3 needs to be larger in area than that first portion 532a of the article 500 in FIG. 2 to provide the same signal clarity. Where there is no direct contact between a user and the conductive portion 532, for example because the section of the conductive portion 532a is located internally, as in FIG. 3, detection of user interaction by the conductive portion may be achieved by a capacitive coupling between due the user and the conductive portion 532. The internal placement of the first portion 532a in the example of FIG. 3 is likely to be more desirable from the user's perspective as the article 500 will have the appearance of a normal consumable. Further, the user will likely more preferably touch a mouthpiece with a "normal appearance" with their lips rather than one with conductive material surrounding the mouthpiece. The conductive material 532 being placed internally, such as in this example, may also contribute to mitigating electrical noise picked up by the conductive material.

Figure 4:
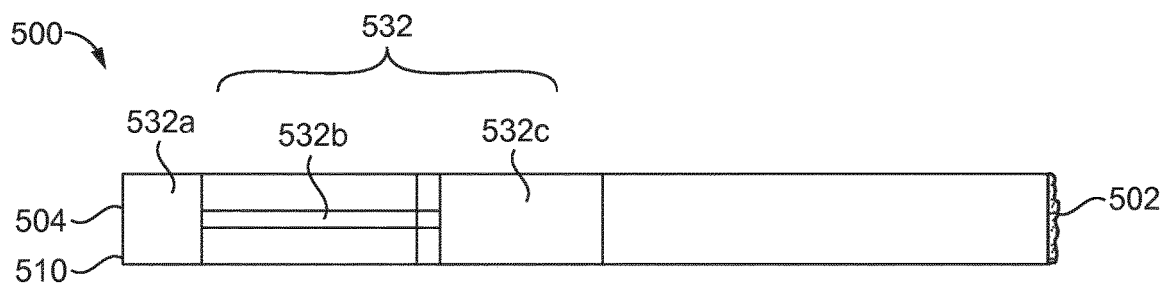
FIG. 4 shows a partial cross-sectional side view of a third example aerosol generating article.

Referring now to FIG. 4, there is shown an example of an article 500 for use with the device 100 of FIG. 1. All three portions 532a, 532b, 532c of the conductive material 532 are externally located in the example shown in FIG. 4. As mentioned above, locating the conductive surface 532 on an external surface of the article 500 improves the signal quality for a comparably sized conductive material 532. This can enable a manufacturer to use less conductive material while still maintaining an acceptable amount of signal during use. The conductive material 532 may be incorporated into an aesthetic element such as design to provide a visually pleasing effect for the user.

Figure 5:
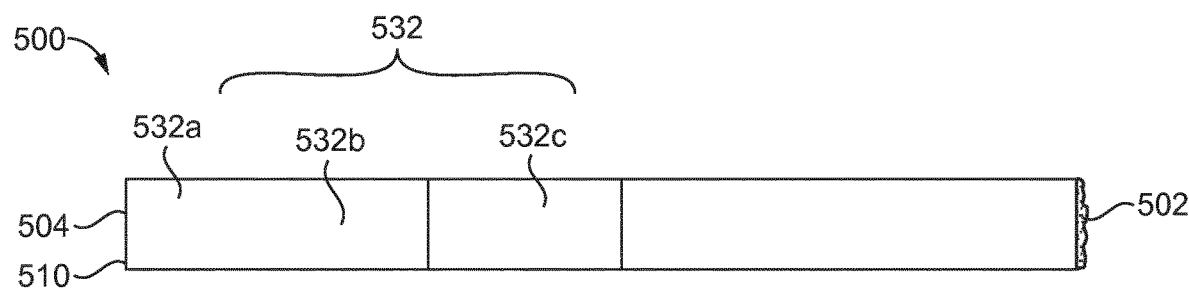
FIG. 5 shows a partial cross-sectional side view of a fourth example aerosol generating article.

Referring now to FIG. 5, there is shown an example of an article 500 for use with the device 100 of FIG. 1. The conductive surface 532 comprises a continuous body rather than a number of portions with distinct sizes or widths as in previous examples. The continuous body is made of a proximal portion 532a, a middle portion 532b and a distal portion 532c and may be arranged on an external surface of the article 500 or arranged internally, for example beneath a paper layer on the outer of the article 500. Where arranged internally a greater area of conductive surface 532 is required to be used to provide an appropriate signal strength to where the conductive material 532 is arranged externally. However, as mentioned above, the internal arrangement may be more visually pleasing for a user. This construction may have several manufacturing advantages as less complex patterns of conductive surfaces need to be provided.

A rod may be heated fairly evenly via heaters 134 that are arranged externally to the rod, such as in the device 100 shown in FIG. 1. Alternatively, the article 500 may be of any shape corresponding to the cavity 131 of the device 100 with which the article 500 is to be used. The only restriction on the shape of the article 500 is that the article 500 should, in use, project from the user to a suitable proximity to the conductive surface 132 in the device 100 so that the conductive material 532 may affect the conductive surface 132.

It should also be appreciated that the conductive surfaces described above do not need to be formed in continuous loops, i.e., they do not need to electrically connect in the circumferential direction of the articles 500. For instance, the conductive surfaces may form partial loops around the outer surface of the article, and define a gap between ends of the conductive surface (e.g., in a horse-shoe type arrangement). However, increasing the angular extent of the conductive surfaces around the surface of the article 500 (or within the article 500 in the case the conductive surface is not on an external surface of the article 500) may be advantageous in permitting a good conductive coupling however the user holds the article 500.

Figure 6:
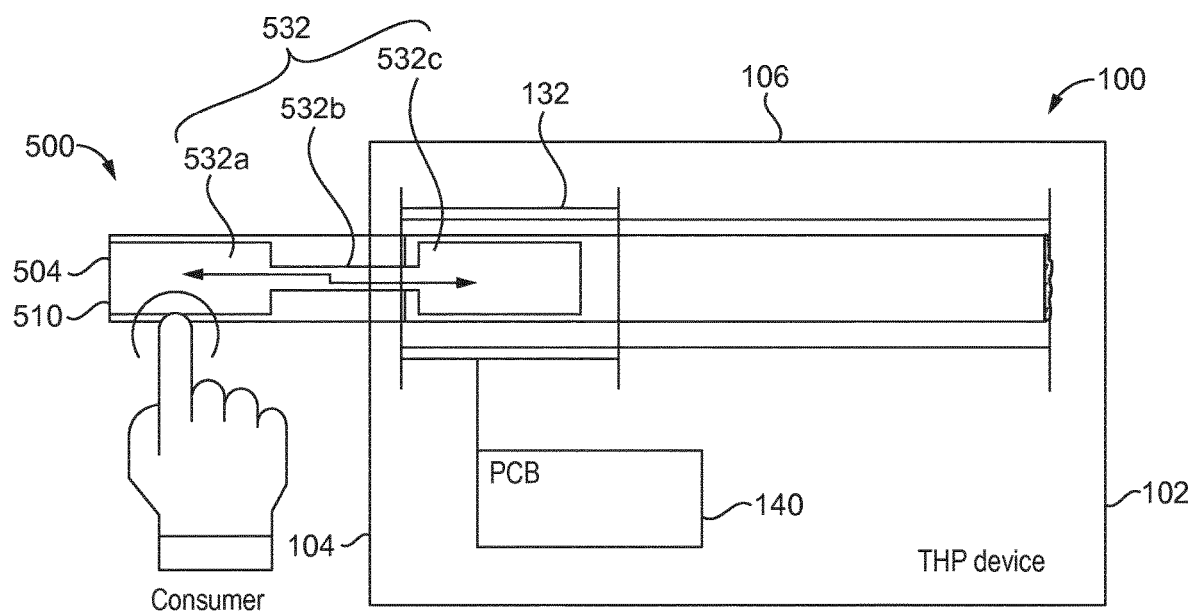
FIG. 6 shows a schematic cross-sectional view of an example aerosol provision device with an aerosol generating article inserted.

Referring now to FIG. 6, there is shown an example of the article 500 in use in a device 100. To improve the cleanliness of the signal detected by the controller 122, suitable materials may be chosen for an outer wall 106 of the device 100. For example, the outer wall 106 could be a conductive material which is connected to the circuit and used to ground the circuit when a user contacts the outer wall 106. The conductive surface 132 may be backed by an insulating material (not shown) in order to improve reliability of the sensing circuit 600. An electrically grounded component (not shown) may be located adjacent a side of the insulating material facing away from the conductive surface 132, and such a component may be grounded by, for example, connection to a conductive outer wall 106 of the device 100.

Figure 7:
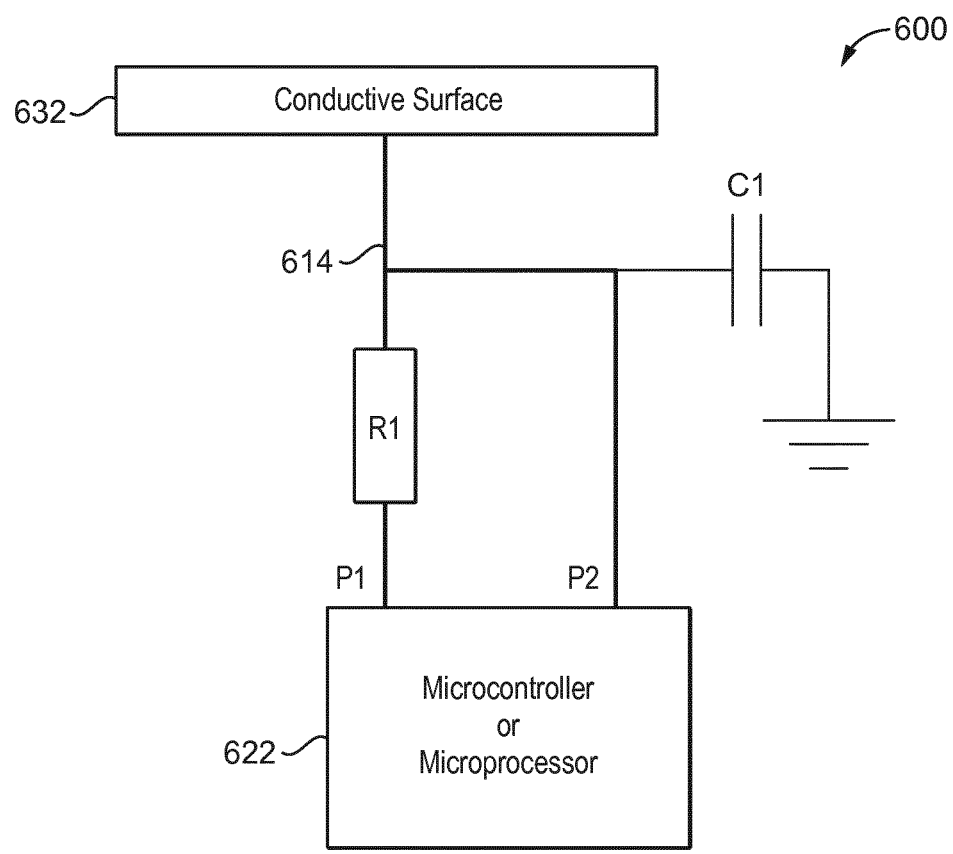
FIG. 7 shows a schematic representation of an example circuit for use in an aerosol provision device according to the present disclosure.

Referring now to FIG. 7, an example circuit 600 for use in the device 100 will be described. The circuit 600 has a number of features shown previously in FIG. 1. Similar features are shown with numerals increased by 500 and discussion of these features will not be repeated here.

The circuit 600 shown in FIG. 7 has a controller 622 for registering a change in an electrical property of the circuit 600, a conductive surface 632 through which a change in an electrical property of the circuit 600 may be affected and conductive elements 614 for connecting the controller 622 to the conductive surface 632. The controller 622 may be a microcontroller or a microprocessor or a timing circuit, which may in some examples be an analogue timing circuit.

The controller 622 has two connection points to the conductive elements 614: a first connection point P1 and a second connection point P2. The circuit 600 also has a resistor R1 arranged between the conductive surface 632 and the first connection point P1 to the controller 622. Optionally the circuit 600 may also have, shown in grey in FIG. 7, a capacitor C1 and an electrical ground 650. Inclusion of the capacitor C1 in the circuit may improve the reliability of the circuit 600 and improve the stability and repeatability of readings provided by the circuit 600.

The controller 622 is able to detect a change in an electrical property of the circuit 600 by toggling a state of first connection point P1 and measuring the time taken for the second connection point P2 to register the changed state. The time taken for this to occur is determined by a time constant that is related to the resistance of resistor R1 and the capacitance of the circuit 600. The circuit 600 is therefore able to detect a change in capacitance of the circuit by detecting a change in the time constant of the circuit.

The capacitance of the circuit 600 includes the capacitance of capacitor C1 (if present) and any additional capacitance present at the conductive surface 632, such as that which exists when a conductive material 532 is placed in close proximity with the conductive surface 632. As discussed above, interaction of a user with the conductive material 532 changes the capacitance at the conductive surface 132 and the conductive material 532.

A change in capacitance for example (a change to C0) due to insertion of an article 500 or for example (a change to C2) due to user interaction with the conductive material 532 is therefore detected by controller 622 as a change in the time constant of the circuit 600. That is, a change in capacitance due to insertion of an article 500 or user interaction with the conductive material 532 (such as by contact with the article 500 by the fingers of mouth of the user) alters the time taken for the second connection point P2 to register a change in state. The controller 622 may note the time taken and can compare it to a database of time periods, which the controller 622 may comprise or which may be provided as a separate component of the circuit 600. Values in the database may, for example, represent pre-determined time periods associated with approved articles for use with the device 100. When the time period taken for the state change to be registered is equal, within some pre-determined acceptable boundaries, to a pre-determined time period, the controller 622 has received an indication that the received article 500 is approved and may enable the device 100.

The controller 622 may control the toggling of first connection point P1. Toggling may occur prior to the beginning of a usage session, or the controller 622 may toggle the first connection point P1 after a set interval. The controller 622 may be configured to toggle the state of first connection point P1 periodically throughout a usage session. For example, the controller 622 may continue to periodically toggle the state of the first connection point P1 while a puff detector continues to detect that the device 100 is in use. The controller 622 may initially toggle upon request from a user, following insertion of an article 500 into the device 100 in which the circuit 600 is housed, and then at various intervals during the usage session to ensure an approved consumable is being used throughout the usage session. This would prevent activation of the device 100 by an approved consumable which is subsequently replaced in the device 100 by an article which is not approved.

The above embodiments are to be understood as illustrative examples of the disclosure. Further embodiments of the disclosure are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. An aerosol generating device for receiving an aerosol generating article, the aerosol generating device comprising:
an electrical circuit comprising a controller for determining a change in an electrical property of the electrical circuit, wherein the change is caused by a user interacting with an aerosol generating article when the aerosol generating article is received by the aerosol generating device,
wherein the aerosol generating article comprises a conductive material and the change is caused by the user interacting with the conductive material, and
wherein the conductive material comprises a first portion for interacting with the user when the user is in contact with the aerosol generating article and a second portion for electromagnetically interacting with the aerosol generating device.

2. The aerosol generating device according to claim 1, wherein the change in the property of the electrical circuit is caused by the user contacting the aerosol generating article.

3. The aerosol generating device according to claim 1, wherein the change in the property of the electrical circuit is caused by the user contacting, and thereby electrically grounding, the conductive material.

4. The aerosol generating device according to claim 1, wherein the aerosol generating device comprises a first conductive surface and wherein when the aerosol generating article is inserted in the aerosol generating device the first conductive surface and the conductive material together have a capacitance, wherein the change in the property of the electrical circuit comprises a change in the capacitance due to the user interacting with the aerosol generating article.

5. The aerosol generating device according to claim 4, wherein the controller is configured to detect the change in the capacitance by detecting a change in a time constant of the electrical circuit.

6. The aerosol generating device according to claim 5, wherein the controller is configured to detect the change in the time constant of the electrical circuit by toggling a state of a first connection to the controller and measuring a time for a second connection to the controller to register a changed state.

7. The aerosol generating device according to claim 6, wherein the controller is configured to periodically toggle the state of the first connection to detect the change in the capacitance.

8. The aerosol generating device according to claim 1, wherein the controller is configured to enable the aerosol generating device for use when the change in the property of the electrical circuit is detected.

9. The aerosol generating device according to claim 1, wherein the controller is configured to evaluate a detected change in the property of the electrical circuit to provide an indication of whether the aerosol generating article received in the aerosol generating device is of a predetermined type.

10. The aerosol generating device according to claim 9, wherein the controller is configured to compare the detected change to a list of at least one predetermined value to provide an indication of whether the aerosol generating article received in the aerosol generating device is of the predetermined type.

11. The aerosol generating device according to claim 9, wherein at least one of:
the predetermined type is an approved article and the controller is configured to enable the aerosol generating device for use when the detected change in property indicates that the aerosol generating article received in the aerosol generating device is an approved article; or
the predetermined type is an approved article and the controller is configured to prevent use of the aerosol generating device when the detected change in property indicates that the aerosol generating article received in the aerosol generating device is not an approved article.

12. The aerosol generating device according to claim 1, wherein at least one of:
- the controller is configured to determine a length of time that the user is in contact with the aerosol generating article using the change in the property of the electrical circuit; or
- the controller is configured to determine at least one location at which the user is in contact with the aerosol generating article using the change in the property of the electrical circuit.

13. The aerosol generating device according to claim 1, wherein at least one of:
- the conductive material is at least partially arranged at an external surface of the aerosol generating article such that the conductive material may be directly contacted by the user; or
- the conductive material is arranged such that no part of the conductive material is directly contactable by the user.

14. The aerosol generating device according to claim 1, wherein the first portion of the conductive material has a terminus located substantially at a proximal end of the aerosol generating article.

15. The aerosol generating device according to claim 1, wherein the conductive material has at least one narrow portion and at least one broad portion, wherein at least one of the at least one broad portions is arranged towards a proximal end of the aerosol generating article.

16. The aerosol generating device according to claim 15, wherein the first portion comprises a first broad portion arranged at a proximal end of the aerosol generating article for interacting with the user and the second portion comprises a second broad portion which is arranged for interacting with the conductive surface of the aerosol generating device, wherein the first broad portion and second broad portion are connected by the narrow portion.

17. A method of detecting user interaction with an aerosol generating article inserted into the aerosol generating device according to claim 1, the method comprising:
- detecting a change in a property of the electrical circuit when the user interacts with the aerosol generating article.

18. The method according to claim 17, wherein the aerosol generating device comprises a conductive surface and the aerosol generating article comprises a conductive material, and the method comprises detecting a change in a capacitance of the electrical circuit when the user interacts with the conductive material.

19. The method according to claim 17, further comprising comparing the change in the property of the electrical circuit to a list of at least one value, and enabling the aerosol generating device for use when the change to the property of the electrical circuit corresponds with the at least one value.

\* \* \* \* \*